(12) United States Patent
Robinson (10) Patent No.: US 8,603,142 B2
(45) Date of Patent: Dec. 10, 2013

(54) SPINOUS PROCESS FIXATION APPARATUS AND METHOD

(76) Inventor: James C. Robinson, Atlanta, GA (US)

( * ) Notice: Subject to any disclaimer, the term of this patent is extended or adjusted under 35 U.S.C. 154(b) by 43 days.

(21) Appl. No.: 12/960,508

(22) Filed: Dec. 5, 2010

(65) Prior Publication Data
US 2012/0143252 A1 Jun. 7, 2012

(51) Int. Cl.
*A61B 17/70* (2006.01)

(52) U.S. Cl.
USPC .......................................................... 606/249

(58) Field of Classification Search
CPC ............. A61B 17/702; A61B 17/7005; A61B 17/7067; A61B 17/7068
USPC .................................................. 606/248, 249
See application file for complete search history.

(56) References Cited

U.S. PATENT DOCUMENTS

| | | | |
|---|---|---|---|
| 4,657,550 A | 4/1987 | Daher | |
| 5,290,312 A | 3/1994 | Kojimoto | |
| 5,496,318 A | 3/1996 | Howland | |
| 5,860,977 A | 1/1999 | Zucherman et al. | |
| 5,876,404 A | 3/1999 | Zucherman et al. | |
| 6,048,342 A | 4/2000 | Zucherman et al. | |
| 6,068,630 A | 5/2000 | Zucherman et al. | |
| 6,152,926 A | 11/2000 | Zucherman et al. | |
| 6,156,038 A | 12/2000 | Zucherman et al. | |
| 6,183,471 B1 | 2/2001 | Zucherman et al. | |
| 6,312,431 B1 | 11/2001 | Asfora | |
| 6,562,074 B2 | 5/2003 | Gerbec | |
| 6,695,842 B2 | 2/2004 | Zucherman et al. | |
| 7,029,473 B2 | 4/2006 | Zucherman et al. | |
| 7,048,736 B2 | 5/2006 | Robinson | |
| D530,423 S | 10/2006 | Miles | |
| 7,306,628 B2 | 12/2007 | Zucherman et al. | |
| 7,481,839 B2 | 1/2009 | Zucherman et al. | |
| 7,727,233 B2 | 6/2010 | Blackwell et al. | |
| 7,857,815 B2 | 12/2010 | Zucherman et al. | |
| 8,262,697 B2 * | 9/2012 | Kirschman | 606/248 |
| 8,292,927 B2 * | 10/2012 | Rouleau et al. | 606/257 |
| 2005/0143738 A1 | 6/2005 | Zucherman | |
| 2005/0196420 A1 | 9/2005 | Zucherman et al. | |
| 2005/0203624 A1 | 9/2005 | Serhan | |
| 2006/0085070 A1 | 4/2006 | Kim | |
| 2006/0264938 A1 | 11/2006 | Zucherman et al. | |
| 2006/0293662 A1 | 12/2006 | Boyer | |
| 2007/0010813 A1 | 1/2007 | Zucherman et al. | |
| 2007/0093830 A1 | 4/2007 | Zucherman et al. | |
| 2007/0219634 A1 | 9/2007 | Greenhalgh | |
| 2007/0270827 A1 | 11/2007 | Lim | |
| 2007/0276381 A1 | 11/2007 | Butler | |

(Continued)

FOREIGN PATENT DOCUMENTS

EP 1138268 10/2001
EP 2275047 A2 1/2011

(Continued)

*Primary Examiner* — Ellen C Hammond
(74) *Attorney, Agent, or Firm* — FisherBroyles, LLP; Anthony J. DoVale (57) ABSTRACT

An implantable device and method for fixation of spinous processes is presented. The device has first and second spaced plates configured for attachment to portions of adjacent spinous processes. The device also has an implant configured for insertion between two adjacent spinous processes. The method has the steps of assembling the components of the implantable device and otherwise inserting them into position onto, between, and/or adjacent two desired spinous processes.

9 Claims, 10 Drawing Sheets

(56) References Cited

U.S. PATENT DOCUMENTS

| | | |
|---|---|---|
| 2008/0177271 A1 | 7/2008 | Yeh |
| 2008/0183211 A1 | 7/2008 | Lamborne et al. |
| 2008/0306545 A1 | 12/2008 | Winslow |
| 2009/0198338 A1 | 8/2009 | Phan |
| 2009/0254123 A1* | 10/2009 | Pafford et al. ............... 606/254 |
| 2009/0281628 A1 | 11/2009 | Oglaza |
| 2010/0057130 A1 | 3/2010 | Yue |
| 2010/0087923 A1 | 4/2010 | Abdou |
| 2010/0211101 A1 | 8/2010 | Blackwell |
| 2010/0234890 A1 | 9/2010 | Alamin |
| 2011/0022090 A1* | 1/2011 | Gordon et al. ............... 606/249 |
| 2011/0029020 A1* | 2/2011 | Gordon et al. ............... 606/248 |
| 2011/0077687 A1* | 3/2011 | Thompson et al. ........... 606/254 |
| 2011/0160772 A1 | 6/2011 | Arcenio |
| 2012/0016418 A1* | 1/2012 | Chin et al. .................... 606/249 |
| 2012/0101528 A1 | 4/2012 | Souza et al. |
| 2012/0109203 A1* | 5/2012 | Dryer et al. .................. 606/249 |

FOREIGN PATENT DOCUMENTS

| | | |
|---|---|---|
| MX | 2009005457 | 2/2009 |
| WO | 2011094062 A1 | 8/2011 |
| WO | 2012012771 A1 | 1/2012 |

\* cited by examiner

SPINOUS PROCESS FIXATION APPARATUS AND METHOD

FIELD OF THE INVENTION

This invention relates generally to spinal surgery, and more particularly to devices for stabilization of the spine in association with placement of an interbody construct for interbody fusion or the like.

BACKGROUND OF THE INVENTION

Varieties of interbody fusion devices are widely used following partial or total discectomies for stabilization of the spine at the site. Some stabilization devices are anchored to the pedicles. With several systems, the use of the pedicles requires screws or other anchoring devices that occupy significant space and involve muscle dissection and associated work-time for implantation. Nerve root injuries are a well-known potential complication of placement of screws in the pedicles.

The interspinous process devices are designed to increase the interspinous process height, thereby increasing the sagittal cross-sectional area of the foramen, where the nerve roots pass away out of the spine. It is thought that these devices may also unload the facet joints, and perhaps the intervertebral disc. They may limit spinal extension. This backward bending position may be painful for patients with spinal stenosis because it reduces the space available for the nerve roots in the exiting foraminal openings.

In addition to interspinous process implants, interspinous process fixation devices are also common to fix adjacent spinous processes to each other to stabilize the spinal motion-segment as an adjunct to spinal fusion. Current systems include spinous process plates that are fixed with adjacent spinous processes sandwiched therebetween.

SUMMARY

Presented herein is an implantable device for fixation of spinous processes. The device comprises first and second spaced plates configured for attachment to portions of adjacent spinous processes. In one aspect, each plate has a first and second surface, whereby the first surface of the first plate is configured to face the second surface of the second plate.

In another aspect, the device comprises an implant with a first face, an opposed second face, a top portion, and a bottom portion. The implant is configured for insertion between two adjacent spinous processes. In one aspect, the implant is an interbody cage. When positioned, the first face of the implant faces the first surface of the first plate and the second face of the implant faces the second surface of the second plate. In this aspect, the first plate is connected to a portion of the implant substantially adjacent the first face, and the second plate is connected to a portion of the implant substantially adjacent the second face.

In addition to the implantable device described herein, presented herein is a method of fixation of spinous processes of a subject. The method comprises assembling the components of the implantable device (i.e. the first and second plates, and the implant), exposing at least one desired spinous process, inserting the implant between two adjacent spinous processes, joining the first and second plates to the implant with a portion of the spinous processes being therebetween, compressing the plates onto the first and second spinous processes, and maintaining the compression of the plates while affixing the plates with respect to the implant.

Related methods of operation are also provided. Other apparatuses, methods, systems, features, and advantages of the interspinous process device and the method of its use will be or become apparent to one with skill in the art upon examination of the following figures and detailed description. It is intended that all such additional apparatuses, methods, systems, features, and advantages be included within this description, be within the scope of the interspinous process device and the method of its use, and be protected by the accompanying claims.

DESCRIPTION OF THE FIGURES

The accompanying drawings, which are incorporated in and constitute a part of this specification, illustrate certain aspects of the instant invention and together with the description, serve to explain, without limitation, the principles of the invention. Like reference characters used therein indicate like parts throughout the several drawings.

DESCRIPTION OF THE INVENTION

The present invention can be understood more readily by reference to the following detailed description, examples, and claims, and their previous and following description. Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. Those skilled in the relevant art will recognize that many changes can be made to the aspects described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "plate" includes aspects having two or more plates unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

In one aspect, presented herein is an implantable device 10 for fixation of spinous processes. The device comprises first and second spaced plates 100, 200 configured for attachment to portions of adjacent spinous processes. In one aspect, each plate has a first and second surface, whereby the first surface 110 of the first plate 100 is configured to face the second surface 210 of the second plate 200.

In another aspect, the device comprises an implant 300 with a first face 310, an opposed second face 320, a top portion 330, and a bottom portion 340. The implant 300 is configured for insertion between two adjacent spinous processes. In one aspect, the implant is an interbody cage. When positioned, the first face 310 of the implant faces the first surface 110 of the first plate 100 and the second face 320 of the implant faces the second surface of the second plate 200. In this aspect, the first plate is connected to a portion of the implant substantially adjacent the first face, and the second plate is connected to a portion of the implant 300 substantially adjacent the second face.

It is beneficial for the plates to be able to move with respect to the implant in order to adjust to the contour of the portions of the spinous processes onto which they attach. In one aspect, the plates can move polyaxially with respect to the implant. In another aspect, one or both of the first and second plates are pivotally connected to the respective portions of the implant. As such, there exist several options to accomplish this feature.

Figure 1:
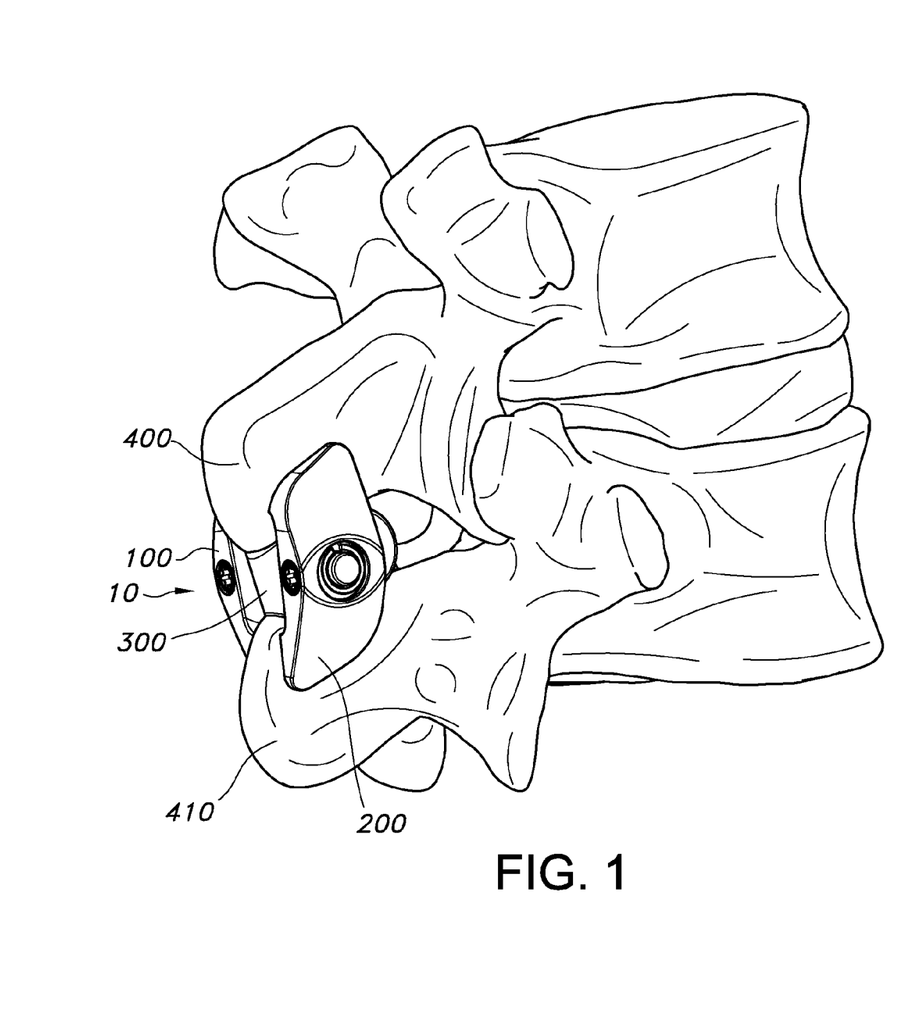
FIG. 1 is a perspective view of one aspect of an implantable device for the fixation of spinous processes, shown in-situ between first and second spinous processes.
Figure 2:
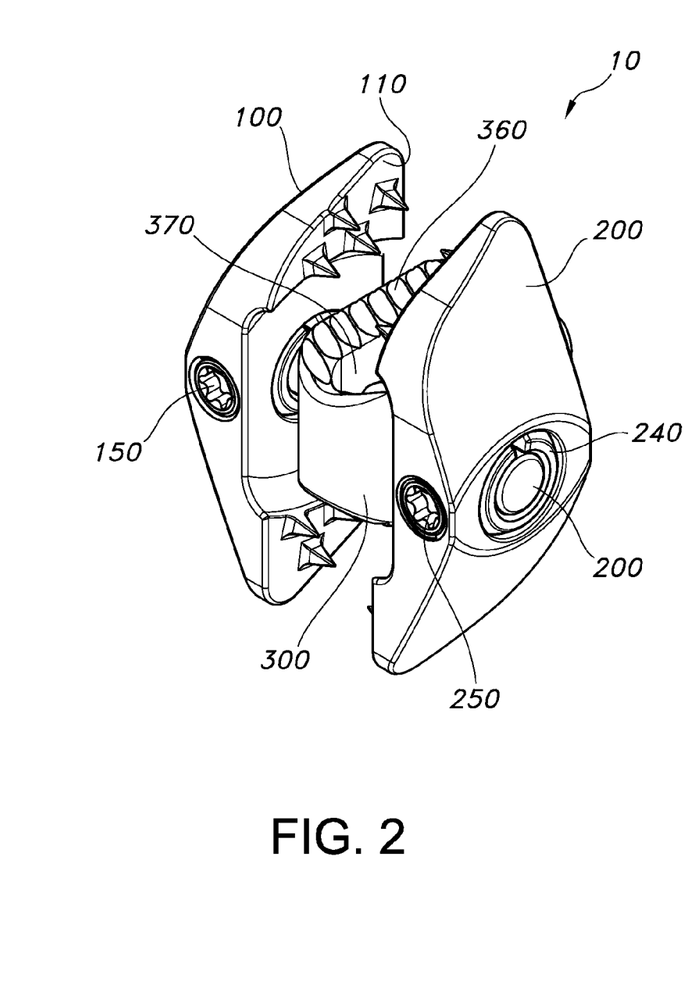
FIG. 2 is a perspective view of one aspect of the implantable device of FIG. 1.
Figure 3:
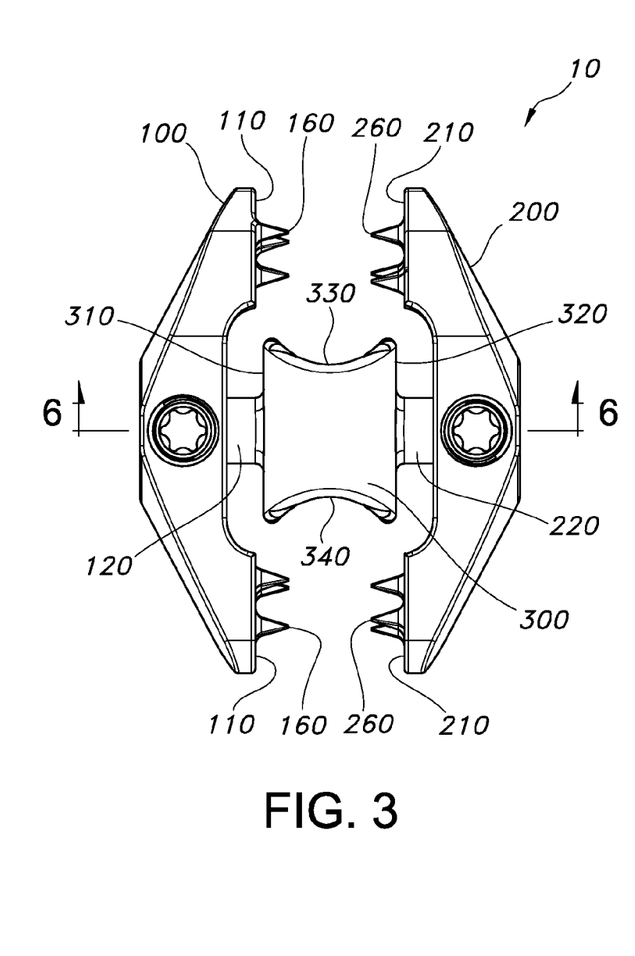
FIG. 3 is a rear elevational view of the implantable device of FIG. 2.
Figure 4:
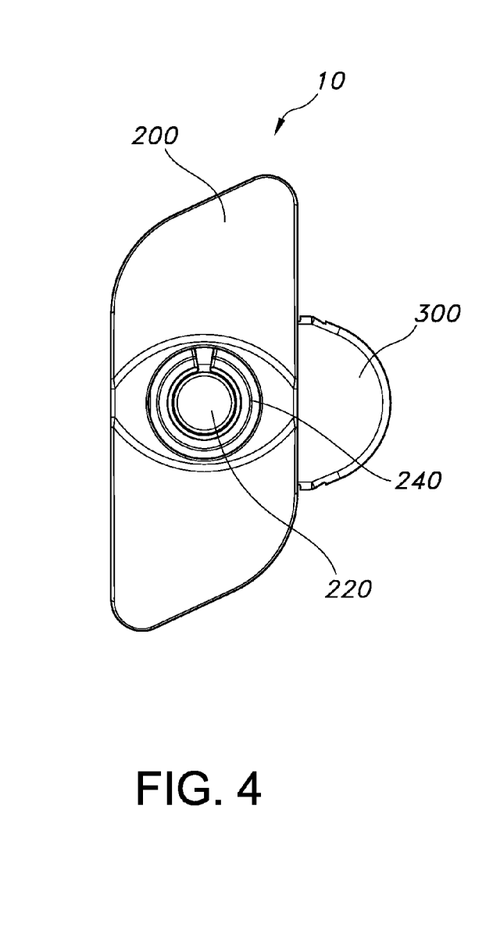
FIG. 4 is right side view of the implantable device of FIG. 2.
Figure 5:
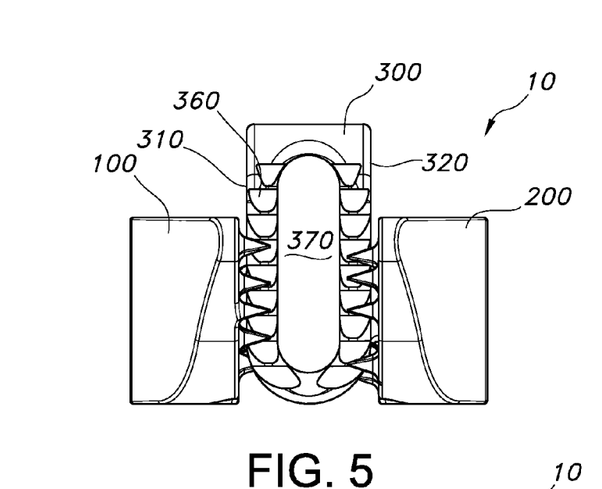
FIG. 5 is a plan view of the implantable device of FIG. 2.
Figure 6:
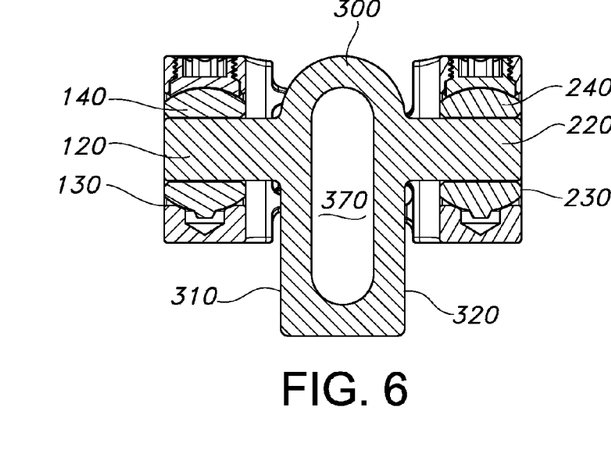
FIG. 6 is cross-sectional bottom elevational view of the implantable device of FIG. 2, cut along line 6-6 in FIG. 3.
Figure 7:
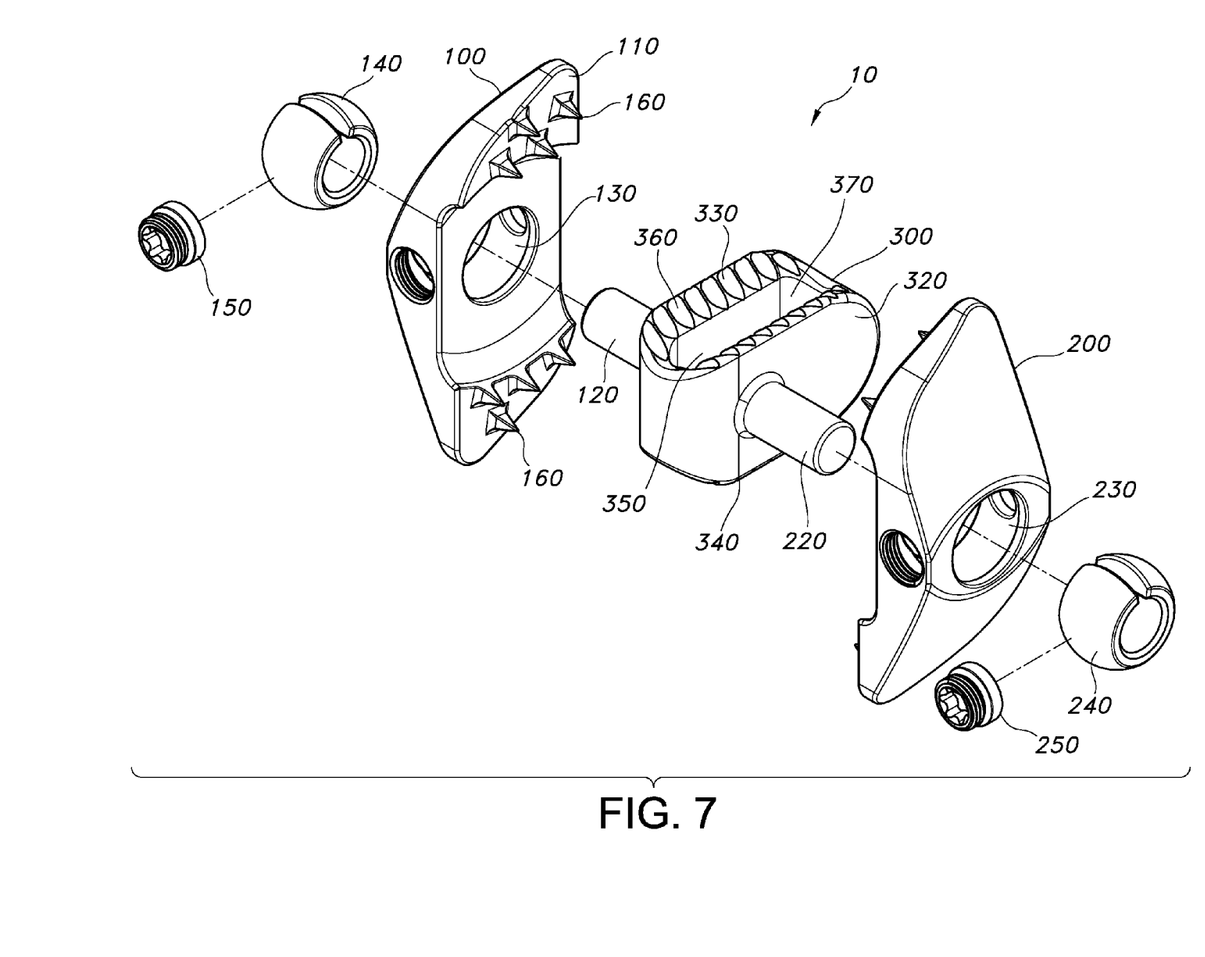
FIG. 7 is an exploded perspective view of the implantable device of FIG. 2.
Figure 8:
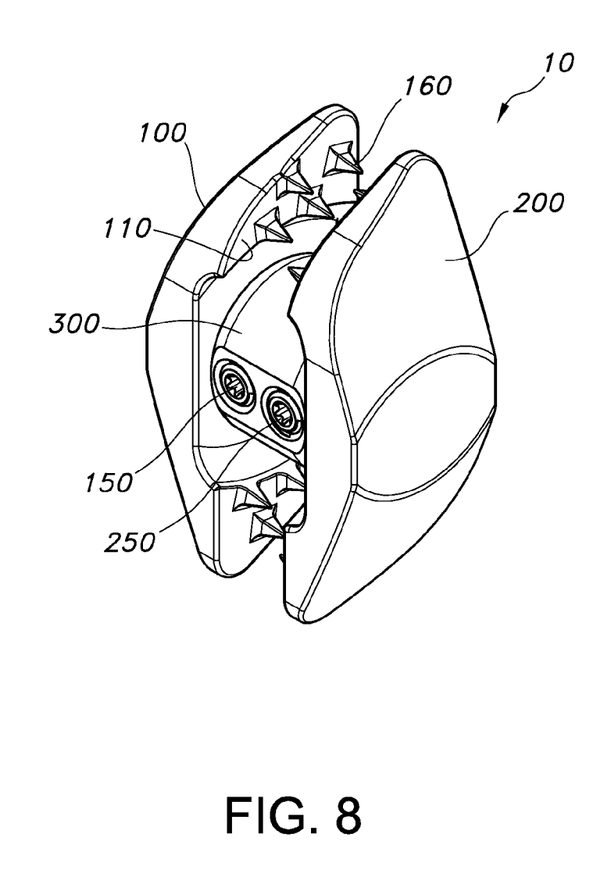
FIG. 8 is a perspective view of one aspect of the implantable device for the fixation of spinous processes.
Figure 9:
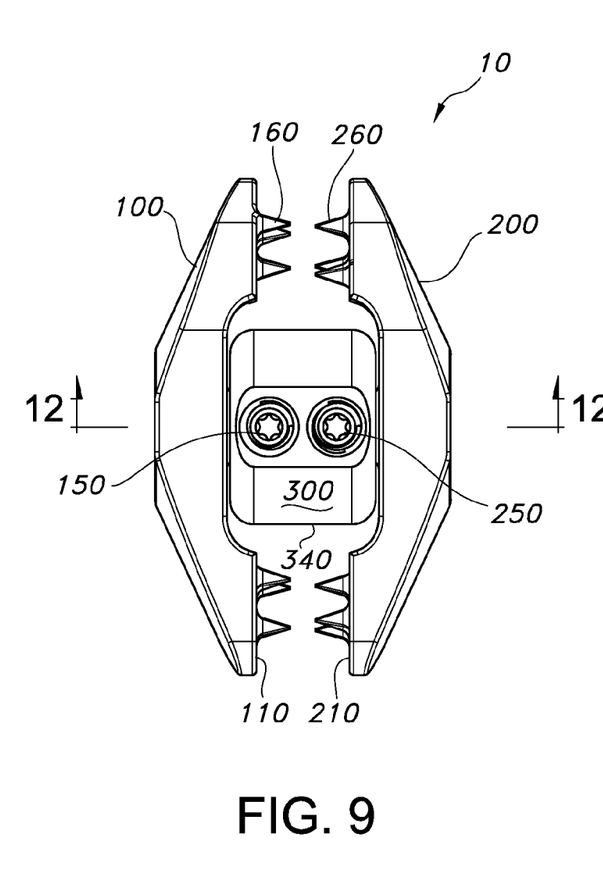
FIG. 9 is a rear elevational view of the implantable device of FIG. 8.
Figure 10:
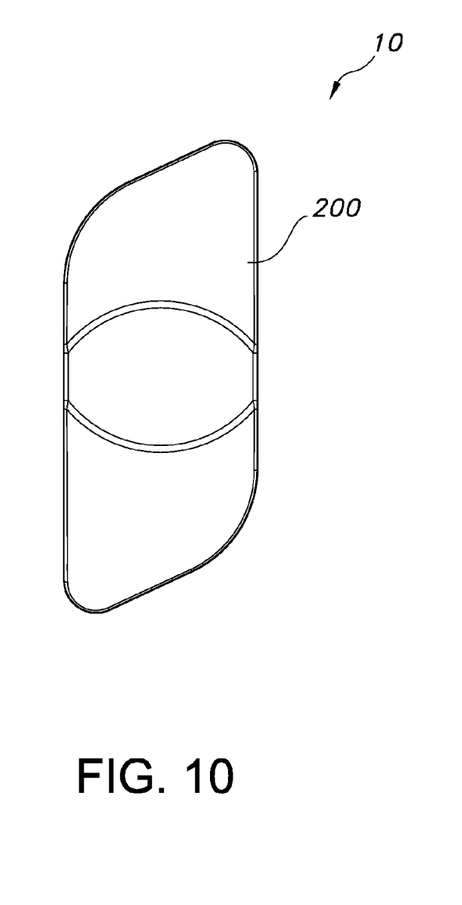
FIG. 10 is right side view of the implantable device of FIG. 8.
Figure 11:
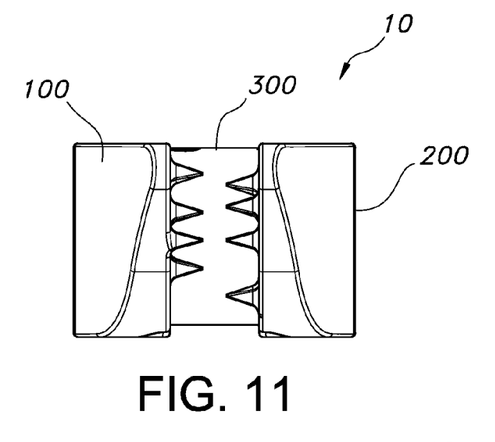
FIG. 11 is a plan view of the implantable device of FIG. 8.
Figure 12:
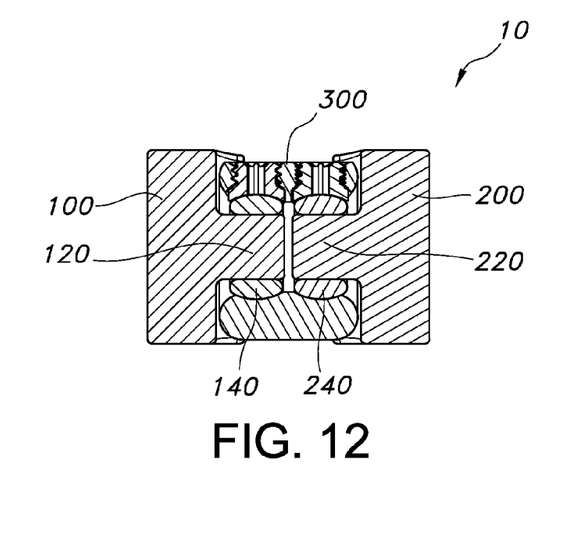
FIG. 12 is cross-sectional bottom elevational view of the implantable device of FIG. 8, cut along line 12-12 in FIG. 9.

In one aspect, the implant comprises a first post 120 projecting therefrom the first face and a second post 220 projecting therefrom the second face. As illustrated in FIG. 7, in one aspect, the first and second posts are substantially normal to the respective first and second faces. However, it is contemplated that the first and second post can be positioned at an acute angle relative to the respective first and second faces of the implant 300.

In another aspect, the first plate comprises a first socket 130 for complimentary receipt of the first post 120 and the second plate 200 comprises a second socket 230 for complimentary receipt of the second post 220. In this aspect, a first internal collar 140 can be positioned within the first socket 130 and a second internal collar 240 can be positioned within the second socket 230. The collars, thus, can be configured to engage a portion of the respective first and second posts. In yet another aspect, each internal collar can be configured to pivot within each respective socket, thereby permitting polyaxial movement of the first and second plates with respect to the implant. The collars can have an external diameter that is larger than the diameter of the socket, thereby resisting movement of the collars into or out of the socket. Additionally, the collars may comprise a slit, which can be compressed for insertion into each socket during manufacturing.

In one exemplified aspect, there can be set screws 150, 250 configured to interface with each collar to tighten the collars thereto the respective first and second posts. The collars are configured to interface at a desired connection point along the particular post with which it interfaces, thereby selectively controlling the distance between the first and second surface of the first and second plates, respectively.

In another aspect, in lieu of, or in addition to, the polyaxial movement permitted by the collar and socket combination, the posts may comprise flexible material, thereby permitting polyaxial movement of the first and second plates with respect to the implant. As such, the plates can be connected thereto the posts without the use of collars, as shown in FIGS. 14-19.

Figure 13:
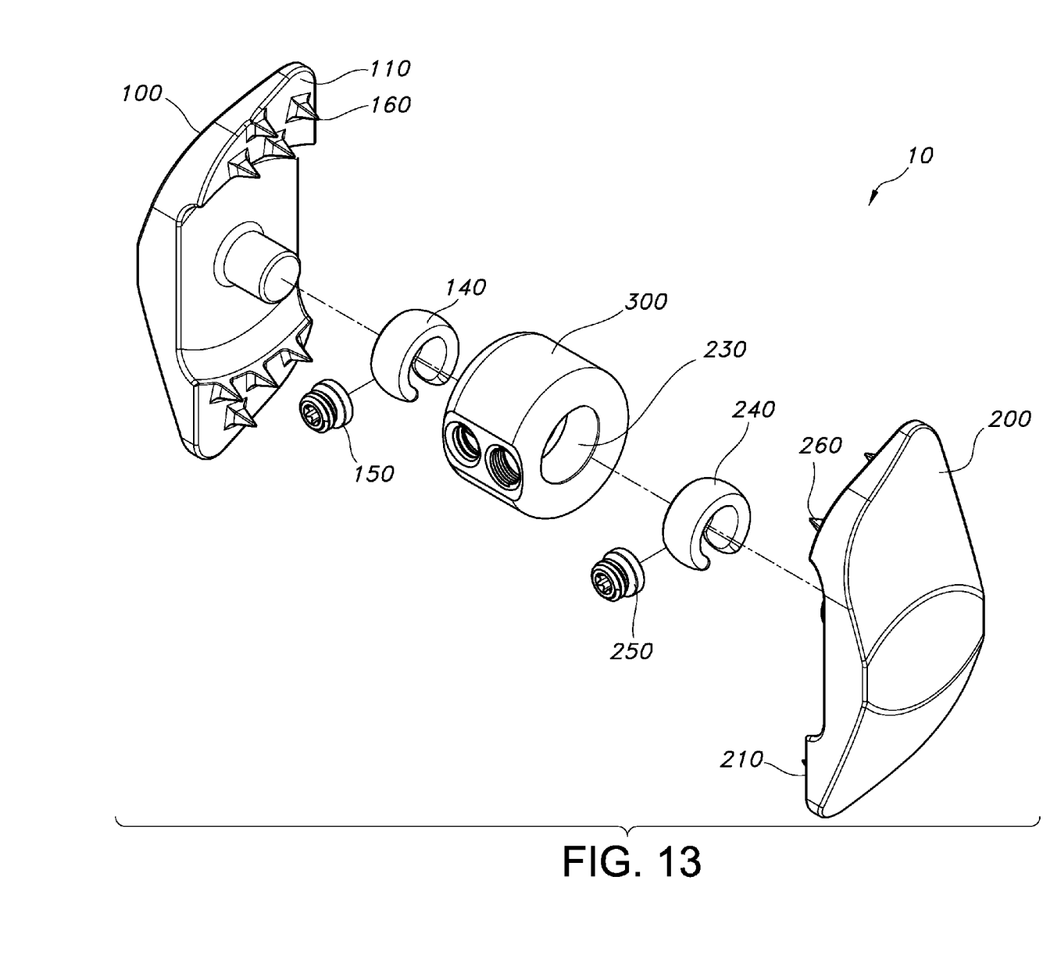
FIG. 13 is an exploded perspective view of the implantable device of FIG. 8.
Figure 14:
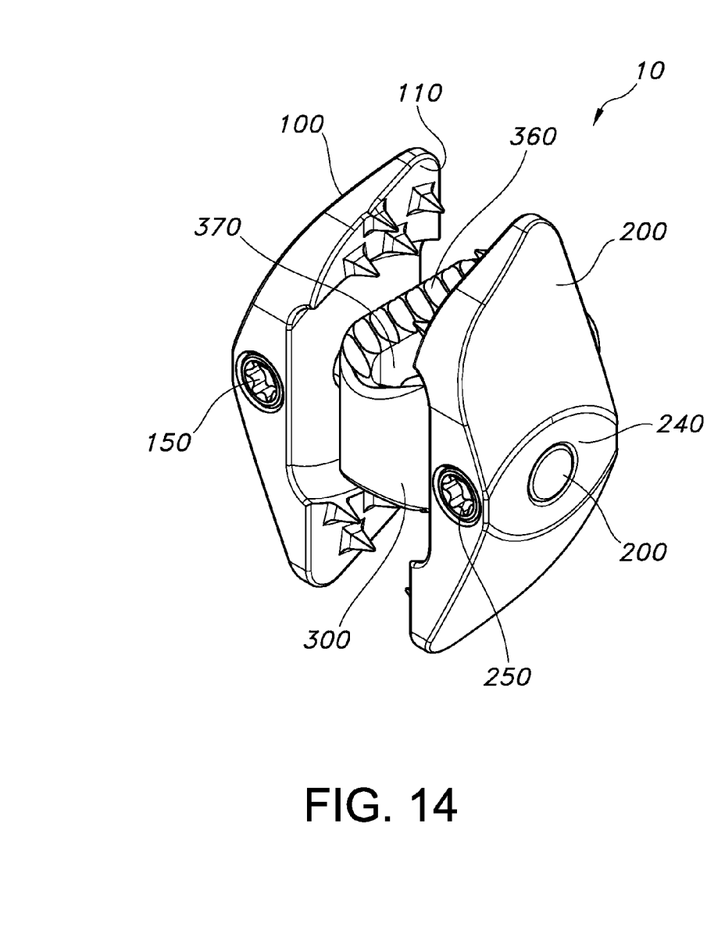
FIG. 14 is a perspective view of one aspect of the implantable device for the fixation of spinous processes showing one aspect with at least one substantially flexible post.
Figure 15:
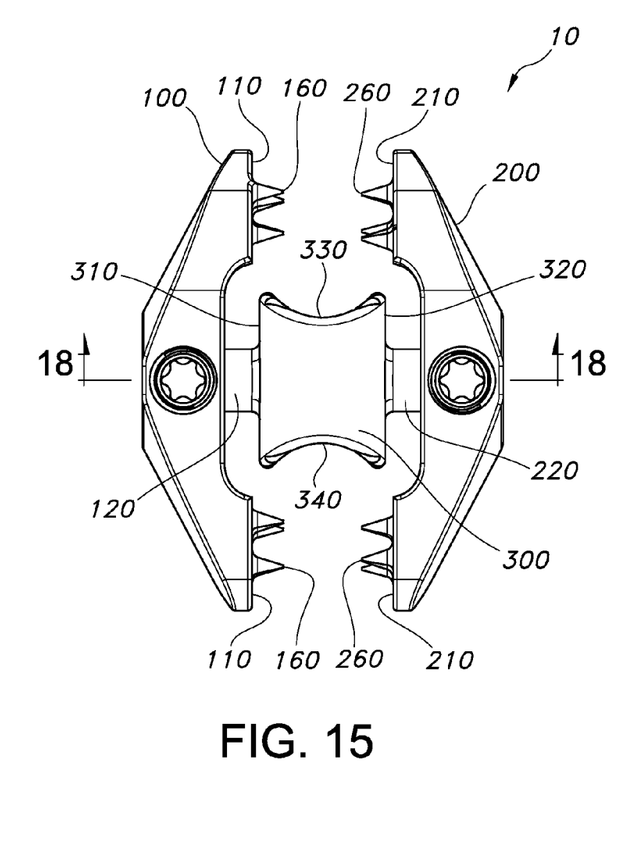
FIG. 15 is a rear elevational view of the implantable device of FIG. 14.
Figure 16:
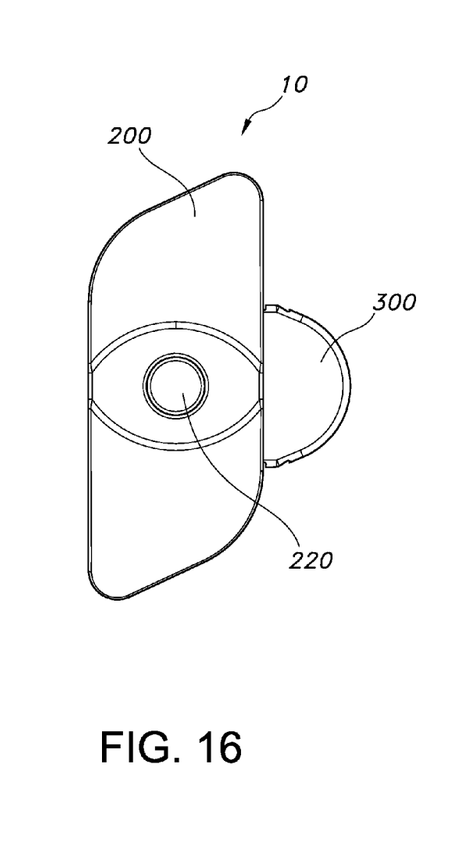
FIG. 16 is right side view of the implantable device of FIG. 14.
Figure 17:
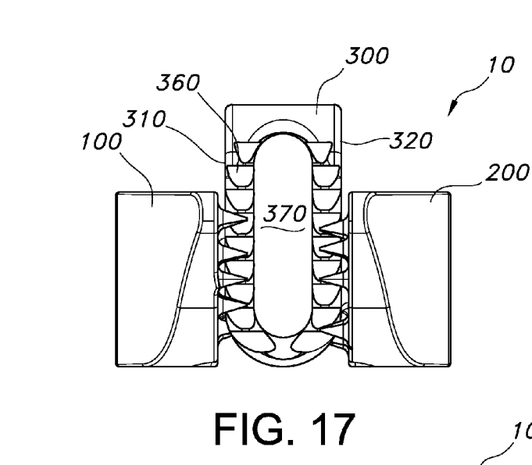
FIG. 17 is a plan view of the implantable device of FIG. 14.
Figure 18:
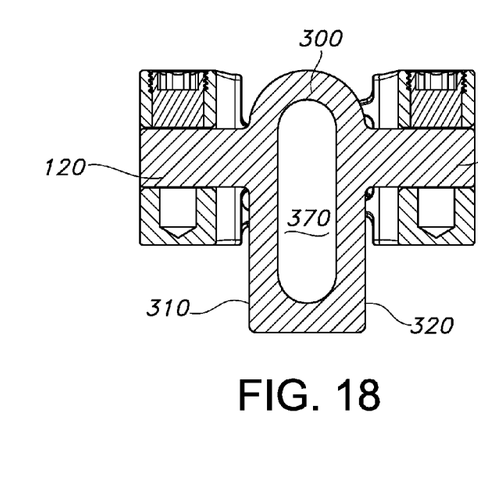
FIG. 18 is cross-sectional bottom elevational view of the implantable device of FIG. 14, cut along line 18-18 in FIG. 15.
Figure 19:
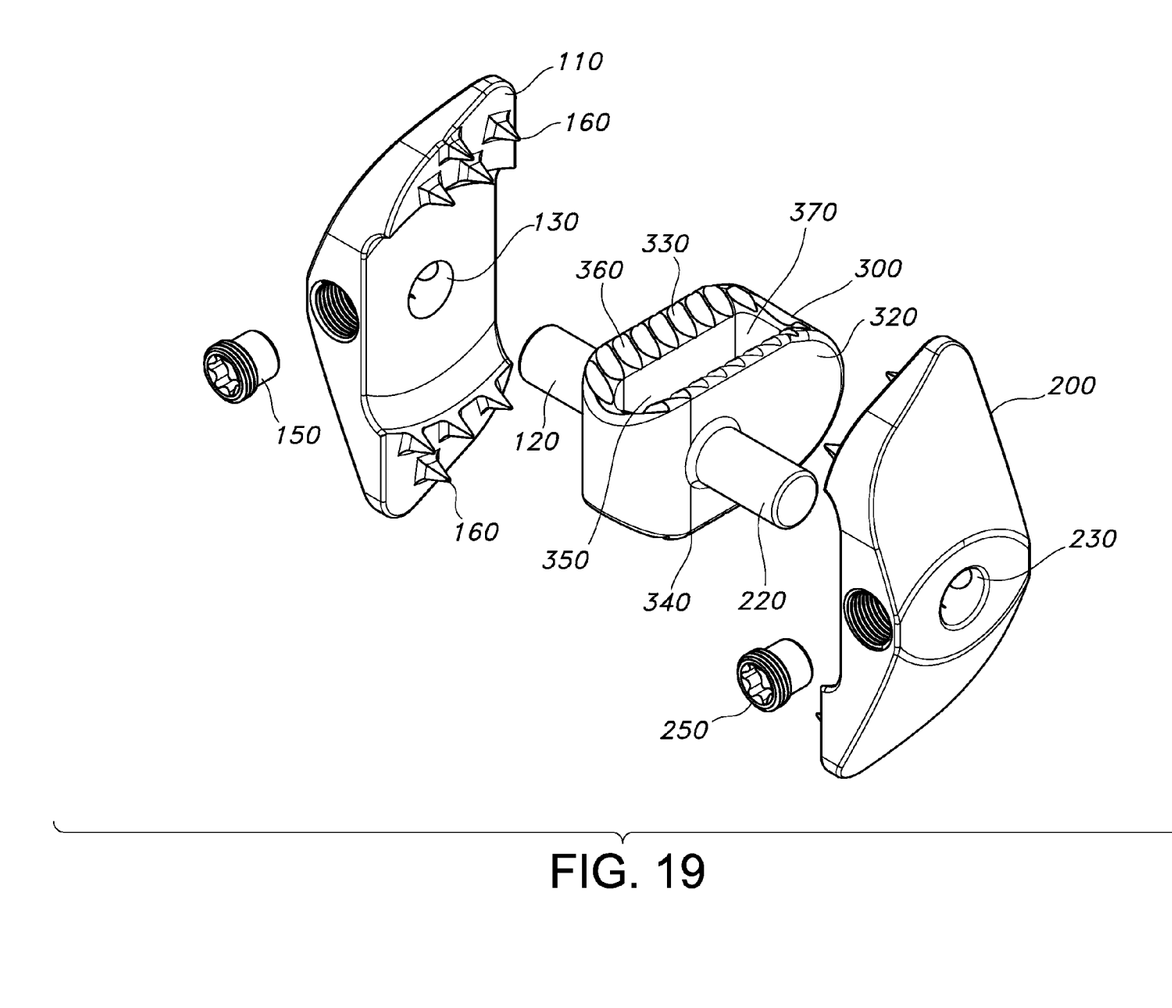
FIG. 19 is an exploded perspective view of the implantable device of FIG. 14.

In another exemplified aspect, as shown in FIG. 13, the posts can project therefrom the first and second surfaces of the first and second plates, respectively, rather than from the first and second faces 310, 320 of the implant. As such, in one aspect, the first and second posts are substantially normal to the respective first and second surfaces. In this aspect, the implant comprises a first socket for complimentary receipt of the first post and a second socket 230 for complimentary receipt of the second post.

Similar to the aspect described above, in another aspect, a first internal collar 140 is positioned within the first socket 130 and a second internal collar 240 is positioned within the second socket. The first and second collars are configured to engage a portion of the respective first and second posts 120, 220. In one aspect, they can engage the posts along the length of the post, thereby allowing for variance in the distance between the two plates.

In one exemplified aspect, each internal collar can pivot within each respective socket, thereby permitting polyaxial movement of the first and second plates with respect to the implant 300. Additionally, as mentioned herein, in another aspect, the first post and the second post are flexible, thereby permitting polyaxial movement of the first and second plates with respect to the implant.

At least one of the first and second surfaces 110, 210 of the plates 100, 200, in one aspect, comprises teeth 160, 260 for frictional engagement of spinous processes. As can be appreciated, both the first and second surfaces can comprise teeth. The teeth 160, 260, for example, engage the spinous processes when the plates are clamped thereon.

In another exemplified aspect, the top portion 330 of the implant defines a longitudinal trough 350 configured for complimentary receipt of a portion of a first spinous process 400. As can be appreciated by one skilled in the relevant art, the bottom portion 340 of the implant may likewise define a longitudinal trough 350 configured for complimentary receipt of a second spinous process 410, which would be adjacent the first spinous process 400.

The longitudinal trough of the top portion can also comprise external edges that have a plurality of consecutive ridges 360 configured for frictional engagement with a portion of the first spinous process. As can be appreciated, the longitudinal trough of the bottom portion may also have external edges with pluralities of consecutive ridges 360 for frictional engagement with a portion of the second spinous process 410. For ease of insertion, the implant can also comprise a tapered distal nose, as illustrated in FIG. 7.

As can be appreciated by one skilled in the art, at times, it can be beneficial to have, in addition to the mechanical fixation, a fusion or other bonding component of the implantable device explained herein. In one exemplified aspect, the implant 300 defines an internal cavity 370 in communication with at least one of the top portion and the bottom portion. In another aspect, the internal cavity 370 is in communication with both the top portion and the bottom portion. In use, the professional may introduce bone cement or bone graft material into the internal cavity to assist in fusion or bonding of the implant with the surrounding spinous processes.

In addition to the implantable device described herein, presented herein is a method of fixation of spinous processes of a subject. The method comprises assembling the components of the implantable device into an implant assembly (i.e. the first and second plates, and the implant), exposing at least one desired spinous process, inserting the implant 300 between two adjacent spinous processes, joining the first and second plates to the implant with a portion of the spinous processes being positioned therebetween, compressing the plates onto the first and second spinous processes, and maintaining the compression of the plates while affixing the plates with respect to the implant.

As mentioned herein, the implant can comprise a first and second post extended therefrom the first and second faces of the implant 300, each post configured for engagement with the first and second plates. In this aspect, the step of joining the first and second plates with the implant can comprise sliding the first plate 100 onto the first post 120 and the second plate 200 onto the second post whereby portions of the first and second spinous processes are positioned in a space between the first and second surfaces and affixing the first plate to the first post and the second plate to the second post. Where the first and second plates comprise collars with set screws, affixing the first and second plates onto the first and second posts can comprise merely tightening the set screws.

In one aspect of the method, the method comprises the step of angulating one or both of the first and second plates relative to each other in at least one plane during compression on the spinous process. In another aspect, the method comprises angulating the two plates in two planes during compression of the plates onto the spinous processes. In an exemplified aspect, the two planes are the coronal and axial planes.

As described, in one aspect, the implant defines an internal cavity in communication with its top and bottom portions. In another aspect, the method further comprises introducing bone graft material into the internal cavity, where the material is selected from the group consisting of autologous bone, allograft bone, bone substitute, and osteoinductive agent. In still another aspect, the method comprises introducing bone cement into the internal cavity.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described invention.

What is claimed is:

1. An implantable device for fixation of spinous processes, comprising:
   first and second spaced plates, each comprising a collar pivotally positioned within a socket, the first plate having a first surface facing a second surface of the second plate; and
   an interbody cage comprising a first post extending from a first face and a second post extending from an opposing second face, the first and second posts having a longitudinal length, wherein the first plate is configured to be selectively fixedly connected to the first post at a first connection point and the second plate is configured to be selectively fixedly connected to the second post at a second connection point and, wherein the first and second connection points can be positioned along the longitudinal length of the first and second posts such that a distance between the first surface and the second surface can be varied without changing the longitudinal length of the first and second posts, and wherein, when the first and second plates are connected to the first and second posts, the first and second plates can move polyaxially with respect to each other.

2. The implantable device of claim 1, wherein a top portion of the interbody cage defines a longitudinal trough configured for complimentary receipt of a portion of a first spinous process.

3. The implantable device of claim 2, wherein a bottom portion of the interbody cage defines a longitudinal trough configured for complimentary receipt of a second spinous process, which is adjacent the first spinous process.

4. The implantable device of claim 2, wherein the longitudinal trough of the top portion has external edges that have a plurality of consecutive ridges configured for frictional engagement with a portion of the first spinous process.

5. The implantable device of claim 3, wherein the longitudinal troughs of the top and bottom portions have external edges that have pluralities of consecutive ridges configured for frictional engagement with a portion of the respective first and second spinous processes.

6. The implantable device of claim 1, wherein the interbody cage comprises a tapered distal nose.

7. The implantable device of claim 1, wherein the interbody cage has a top portion and an opposed bottom portion and defines an internal cavity in communication with at least one of the top portion and the bottom portion.

8. The implantable device of claim 1, wherein the interbody cage has a top portion and an opposed bottom portion and defines an internal cavity in communication with the top portion and the bottom portion.

9. The implantable device of claim 1, wherein the posts and the interbody cage are integral.

* * * * *